(12) United States Patent
Wu et al.

(10) Patent No.: US 12,270,807 B2
(45) Date of Patent: Apr. 8, 2025

(54) REACTING DEVICE OF DUAL PATH SYNCHRONOUS IMMUNOCHROMATOGRAPHIC PLATFORM AND IT'S USING METHOD

(71) Applicant: Taichung Veterans General Hospital, Taichung (TW)

(72) Inventors: Ming-Feng Wu, Taichung (TW); Hui-Chun Chang, Taichung (TW); Jing-Lian Jheng, Taichung (TW); Yi-Yun Hung, Taichung (TW); Jen-Ying Li, Taichung (TW); Hui-Chen Chen, Taichung (TW); Jiunn-Min Wang, Taichung (TW)

(73) Assignee: TAICHUNG VETERANS GENERAL HOSPITAL, Taichung (TW)

( * ) Notice: Subject to any disclaimer, the term of this patent is extended or adjusted under 35 U.S.C. 154(b) by 765 days.

(21) Appl. No.: 17/367,414

(22) Filed: Jul. 4, 2021

(65) Prior Publication Data
US 2022/0011299 A1 Jan. 13, 2022

(30) Foreign Application Priority Data
Jul. 8, 2020 (TW) ................................. 109123103

(51) Int. Cl.
*G01N 33/53* (2006.01)
*G01N 33/543* (2006.01)

(52) U.S. Cl.
CPC ... *G01N 33/5304* (2013.01); *G01N 33/54389* (2021.08)

(58) Field of Classification Search
CPC ..... B01L 2300/0672; B01L 2300/0825; B01L 2300/0864; B01L 2400/0683; B01L 3/5023; G01N 33/5304; G01N 33/54389
See application file for complete search history.

(56) References Cited

U.S. PATENT DOCUMENTS

| | | | |
|---|---|---|---|
| 6,565,808 B2 * | 5/2003 | Hudak | B01L 3/5023 422/417 |
| 8,449,835 B2 | 5/2013 | Wu | |
| 2004/0184954 A1 * | 9/2004 | Guo | B01L 3/5023 422/400 |
| 2012/0188378 A1 * | 7/2012 | Hsiao | G01N 21/274 382/218 |

* cited by examiner

Primary Examiner — Kristina M Deherrera
Assistant Examiner — Gedeon M Kidanu
(74) Attorney, Agent, or Firm — Cheng-Ju Chiang

(57) ABSTRACT

A reacting device of dual path synchronous immunochromatographic platform includes a seat, an upper housing, and a fluid dividing funnel. The seat contains two immunochromatographic carriers. The hollow pipe portion has two sloped structures. A force bearing portion of the fluid dividing funnel can be pressed down, so two fluid exits of the fluid dividing funnel move towards these two sloped structures. The specimen drops and is guided into these two immunochromatographic carriers respectively. A reaction result can be observable. The fluid dividing funnel can divide the specimen into two immunochromatographic carriers evenly. The sloped structure can increase the accuracy of specimen supply. Excess specimen can be scraped off for enhancing the solving accuracy. In addition, it can decrease the possibility of false positive problem.

2 Claims, 14 Drawing Sheets

REACTING DEVICE OF DUAL PATH SYNCHRONOUS IMMUNOCHROMATOGRAPHIC PLATFORM AND IT'S USING METHOD

FIELD OF THE INVENTION

1. Field of the Invention

The present invention relates to a reacting device of dual path synchronous immunochromatographic platform and it's using method. Particularly, the fluid dividing funnel can divide the specimen into two immunochromatographic carriers evenly. The sloped structure can increase the accuracy of specimen supply. Excess specimen can be scraped off for enhancing the solving accuracy. In addition, it can decrease the possibility of false positive problem.

2. Description of Related Art

A traditional single-strip immunochromatographic test paper only obtains one threshold for a specific reacting object. The specimen must be collected and check the volume of the specimen by the user before conducting such immunochromatographic test. After which, the specimen (or mixed with certain solvent) can be imported into the traditional testing device. Then, the result can be observed by the user's eyes. However, the single-strip type tester only has the result of qualitative analysis. If two or more control lines are disposed on the single-strip immunochromatographic test paper or using two test papers, it seems to be possible to conduct a semi-qualitative analysis.

Besides, for the same specimen, its concentration will be influenced by the gravity. The higher concentration portion will stay in the lower part of the specimen container. As a result, the specimen near the bottom will drop down first. After dropping a while, the later drops will have less concentration. Thus, it will cause the chemical reaction (relating to the threshold) at the control line(s) inaccurate.

In addition, if the volume of the specimen is too much or the user does not check the result during a preset time, the test result will be inaccurate.

SUMMARY OF THE INVENTION

One of objects of the present invention is to provide a reacting device of dual path synchronous immunochromatographic platform and it's using method. In which, the fluid dividing funnel can divide the specimen into two immunochromatographic carriers evenly. The sloped structure can increase the accuracy of specimen supply. Excess specimen can be scraped off for enhancing the solving accuracy. In addition, it can decrease the possibility of false positive problem. Particularly, it can solve the traditional problems such as the traditional single-strip immunochromatographic test paper only obtains one threshold for a specific reacting object; for the same specimen, its concentration will be influenced by the gravity; and if the volume of the specimen is too much or the user does not check the result during a preset time, the test result will be inaccurate.

In order to overcome the traditional problems, the present invention is provided as a technical solution.

The present invention relates to a reacting device of dual path synchronous immunochromatographic platform comprising:

a seat having a first slot and a second slot, the first slot being provided for receiving a first immunochromatographic carrier, the second slot being provided for receiving a second immunochromatographic carrier;

an upper housing disposed on the seat, the upper housing including a first window, a second window, a hollow pipe portion, a first end, and a second end; the first window, the second window and the hollow pipe portion being positioned between the first end and the second end, the first window being disposed on the first slot; the second window being disposed on the second slot; the hollow pipe portion being adjacent to the first end and having a top opening, a securing protrusion, an inner space, a first sloped structure, and a second sloped structure; and a fluid dividing funnel being secured on the securing protrusion through the top opening and extending into the inner space, the fluid dividing funnel having a fluid entrance, a first diversion channel, a second diversion channel, and a force bearing portion; the first diversion channel being disposed on and guided to the first sloped structure, the first diversion channel having a first fluid exit; the second diversion channel being disposed on and guided to the second sloped structure, the second diversion channel having a second fluid exit; the force bearing portion being disposed between the first diversion channel and the second diversion channel;

wherein a specimen is imported into the fluid entrance and the force bearing portion is pressed down so that the first fluid exit and the second fluid exit move towards the first sloped structure and the second sloped structure respectively and the first fluid exit and the second fluid exit being effectuated to deform and slide so as to extend out portionally; the specimen drops from the first fluid exit and the second fluid exit to the first immunochromatographic carrier and the second immunochromatographic carrier respectively; and a reaction result is observable from the first window and the second window respectively.

In addition, a using method of reacting device of dual path synchronous immunochromatographic platform comprising:

[1] preparing step;
[2] importing specimen and reacting step;
[3] time counting and taking photo step; and
[4] obtaining result step.

DETAILED DESCRIPTION OF THE INVENTION

Figure 1:
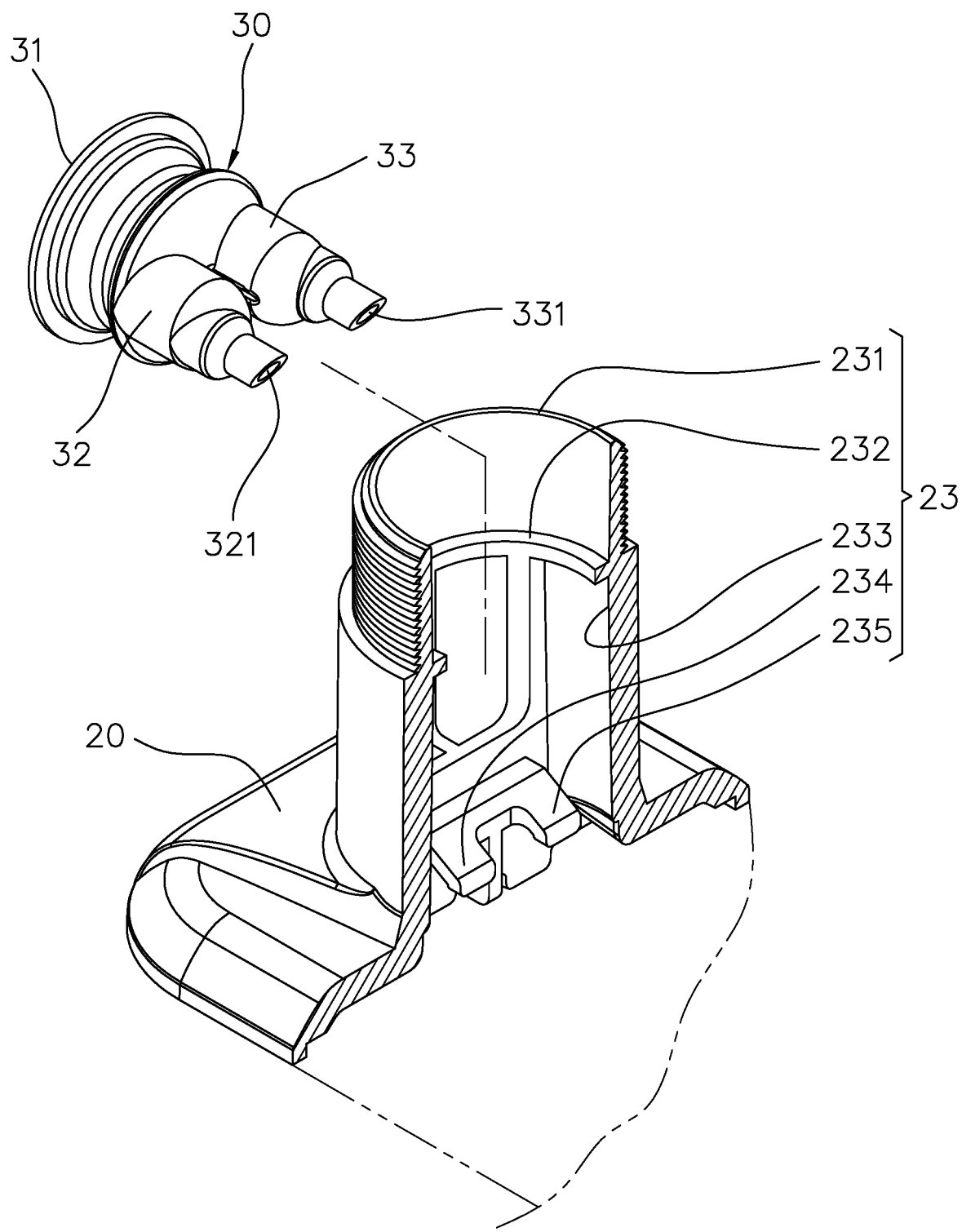
FIG. 1 is a view illustrating a portion of the first preferred embodiment of the present invention.
Figure 2:
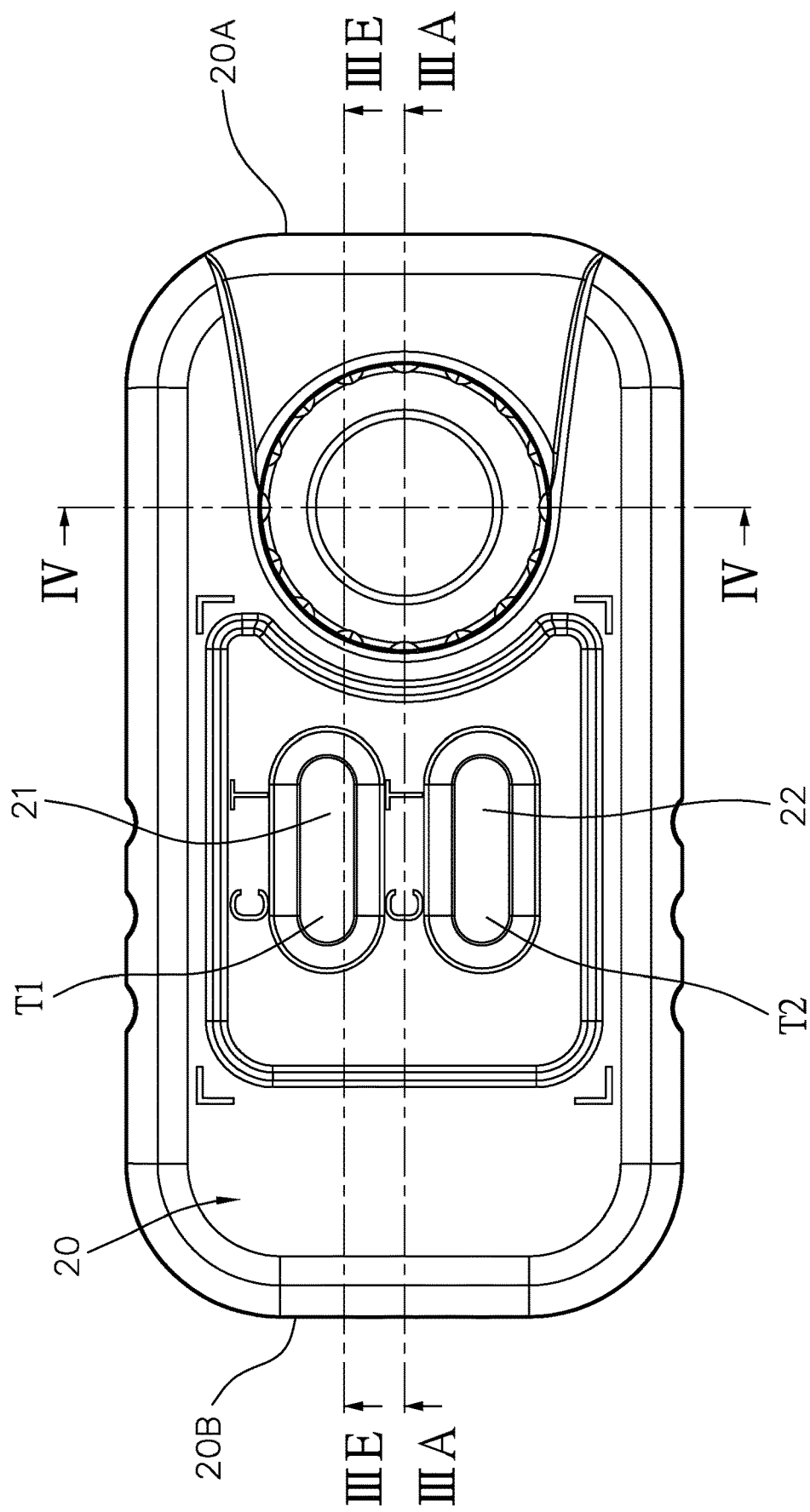
FIG. 2 is a top view of the first preferred embodiment of the present invention.

FIGS. 1, 2, 3A, 3B, 3C, 3D, 3E, and 4 illustrate an exemplary embodiment of this invention. This invention relates to a reacting device of dual path synchronous immunochromatographic platform and it's using method. About the reacting device, it mainly includes a base 10, an upper housing 20, and a fluid dividing funnel 30.

With regard to this seat 10, it has a first slot 11 and a second slot 12. The first slot 11 is provided for receiving a first immunochromatographic carrier T1. The second slot 12 is provided for receiving a second immunochromatographic carrier T2.

About this upper housing 20, it is disposed on the seat 10. The upper housing includes a first window 21, a second window 22, a hollow pipe portion 23, a first end 20A, and a second end 20B. The first window 21, the second window 22, and the hollow pipe portion 23 are positioned between the first end 20A and the second end 20B. The first window 21 is disposed on the first slot 11. The second window 22 is disposed on the second slot 12. The hollow pipe portion 23 is adjacent to the first end 20A and the hollow pipe portion 23 has a top opening 231, a securing protrusion 232, an inner space 233, a first sloped structure 234, and a second sloped structure 235.

Concerning the fluid dividing funnel 30, it is secured on the securing protrusion 232 through the top opening 231 and extends into the inner space 233. This fluid dividing funnel 30 has a fluid entrance 31, a first diversion channel 32, a second diversion channel 33, and a force bearing portion 34. The first diversion channel 32 is disposed on and guided to the first sloped structure 234. The first diversion channel 32 has a first fluid exit 321. The second diversion channel 33 is disposed on and guided to the second sloped structure 235. The second diversion channel 33 has a second fluid exit 331. The force bearing portion 34 is disposed between the first diversion channel 32 and the second diversion channel 33.

Hence, a specimen 91 can be imported into the fluid entrance 31. By applying a downward force P (referring to FIG. 3D, from the left to right, showing the change before applying force, during applying force, and after applying the force; a first height H1 is decreased into a second height H2 during the force applying process). The force bearing portion 34 is pressed down, so that the first fluid exit 321 and the second fluid exit 322 move towards the first sloped structure 234 and the second sloped structure 235 respectively. Then, both of the first fluid exit 321 and the second fluid exit 322 are effectuated to deform and slide (on the first sloped structure 234 and the second sloped structure 235) so as to extend out portionally (as illustrated in the right portion of FIG. 3D). Therefore, the specimen 91 can drop from the first fluid exit 321 and the second fluid exit 322 to the first immunochromatographic carrier T1 and the second immunochromatographic carrier T2 respectively. Finally, a reaction result is observable from the first window 21 and the second window 22 respectively.

Practically, the fluid dividing funnel 30 can be a flexible structure.

The first immunochromatographic carrier T1 is preferably a test paper. The second immunochromatographic carrier T2 is preferably a test paper as well. No matter which one, a distal side is disposed with a control area (briefly referred as C, or called a control line) that is embedded with a predetermined object for combining with or reacting with certain target, such as immunoglobulin. Moreover, its near side can be disposed with a test area (briefly referred as T, or called a test line) that is embedded with a predetermined object for combining with or reacting with another preset target, such as protein or antibody.

In this invention, the reacting device can further comprise a pressing element M. It is used for applying a downward force P on the force bearing portion 34 via the top opening 231 and the fluid entrance 31.

Figure 3A:
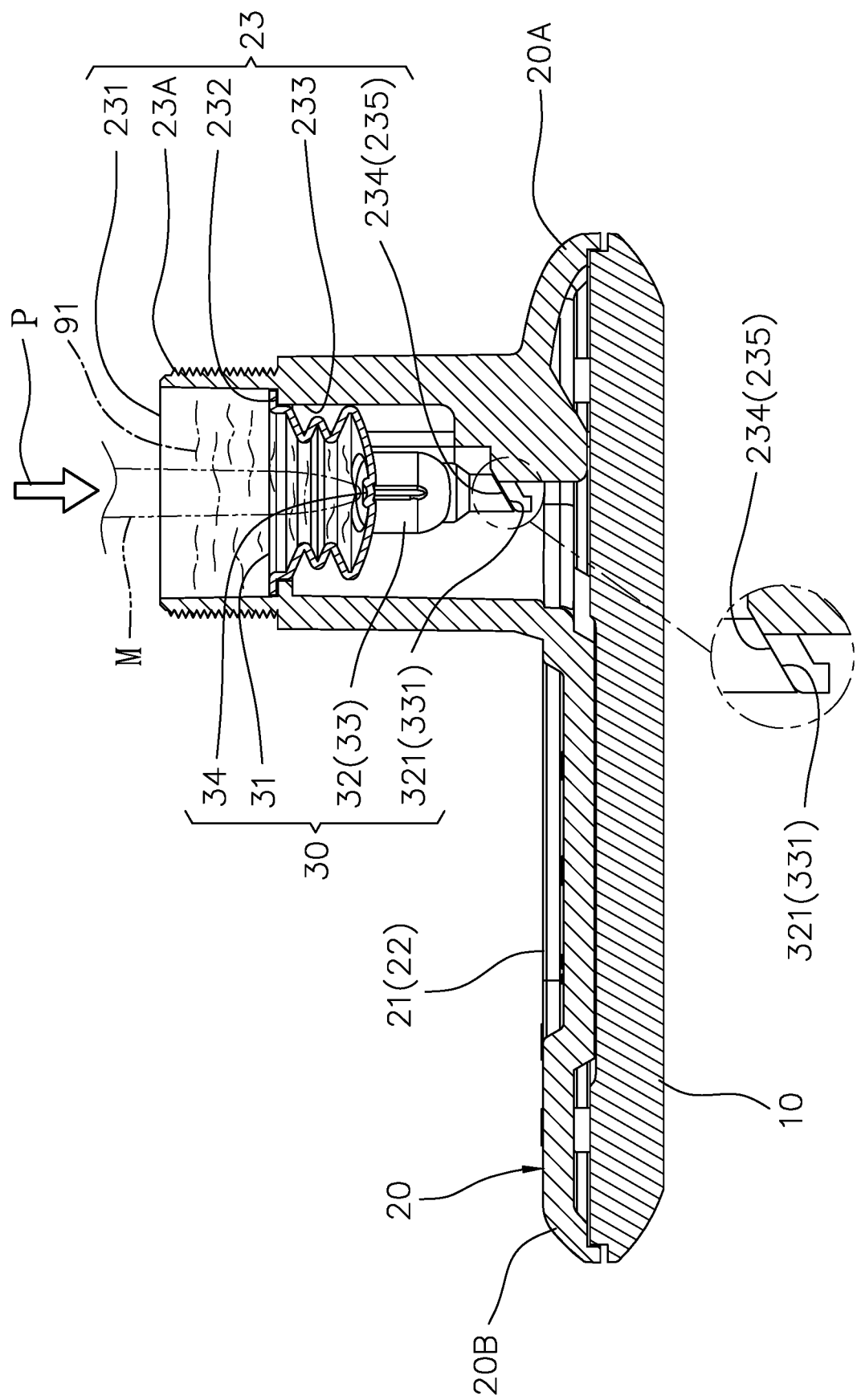
FIG. 3A is a cross-sectional view taken along the line IIIA-IIIA of FIG. 2.
Figure 3B:
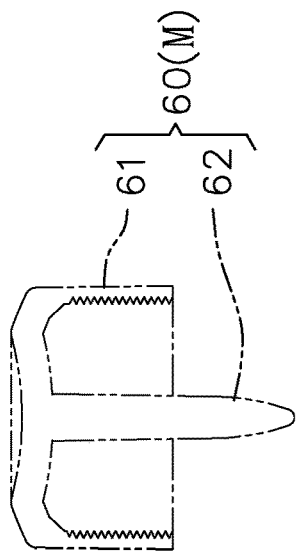
FIG. 3B is a view exhibiting the first exemplary embodiment of a portional structure in FIG. 3A.
Figure 3C:
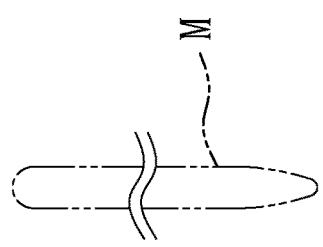
FIG. 3C is a view exhibiting the second exemplary embodiment of a portional structure in FIG. 3A.

As illustrated in FIGS. 3B and 3C, the pressing element M can be selected from an elongated structure (such as a known tongue depressor or a bamboo chopstick) or a sampler 60.

Figure 6A:
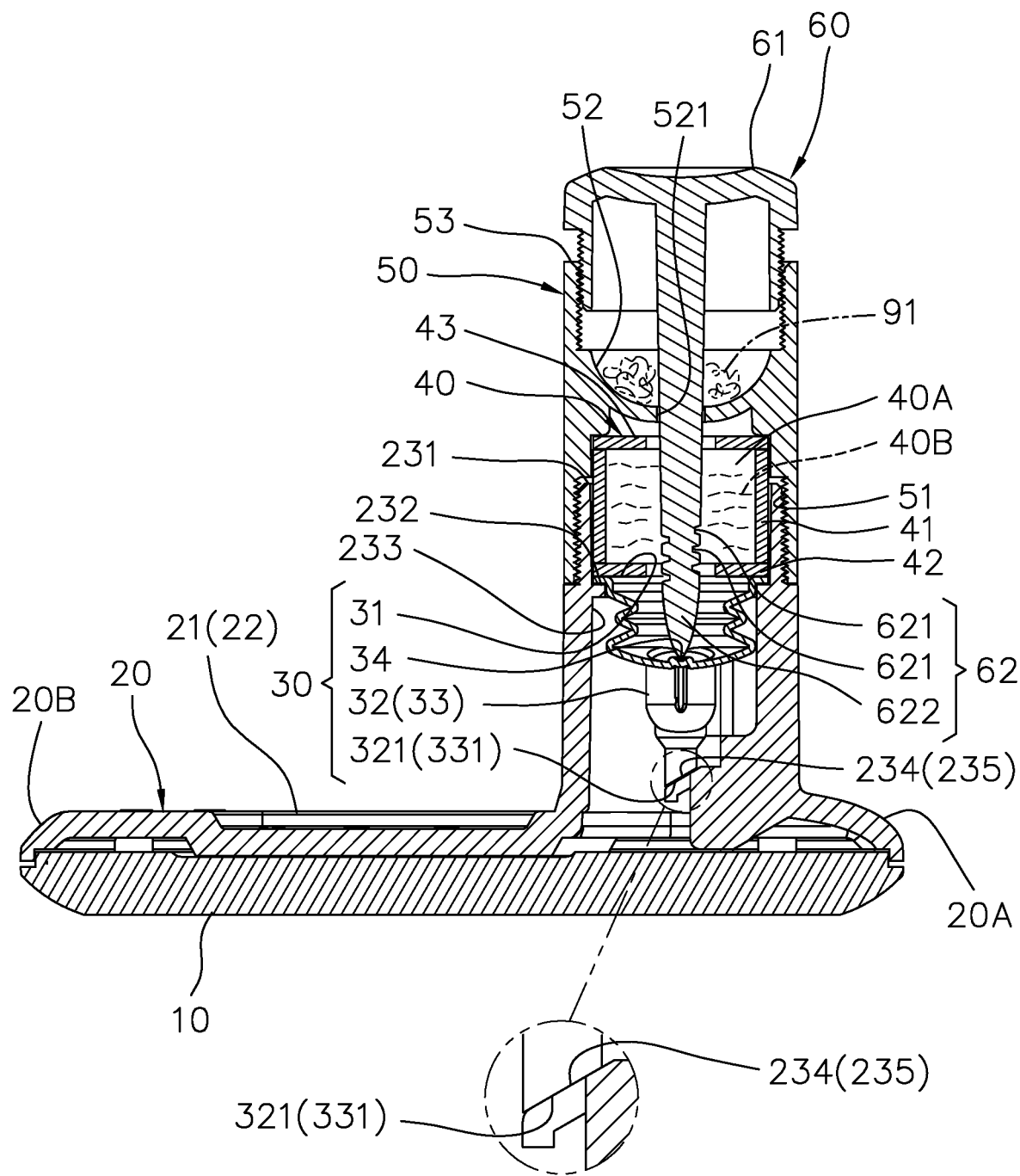
FIG. 6A is a cross-sectional view showing (similar to the viewing direction in FIG. 3A) the assembled structure of the embodiment in FIG. 5.

If the sampler 60 is used, the sampler 60 preferably contains a cover 61 and a sampling rod 62 which is extended from the cover 61 so as to allow for applying the downward force P toward the force bearing portion 34. About the sampling rod 62 (as shown in FIG. 6A), the shape, mode, or length of the sampling rod 62 can be modified into various types for different applications.

Figure 3D:
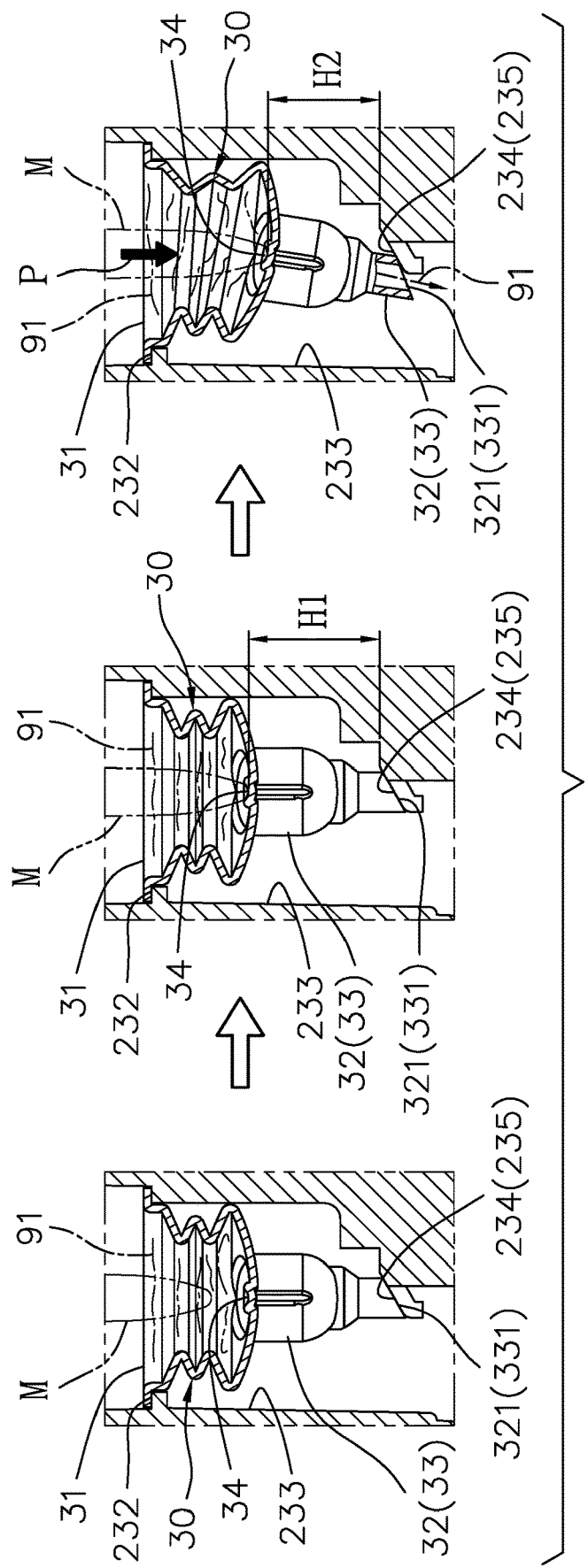
FIG. 3D shows the actual using process of a portional structure in FIG. 3A.
Figure 3E:
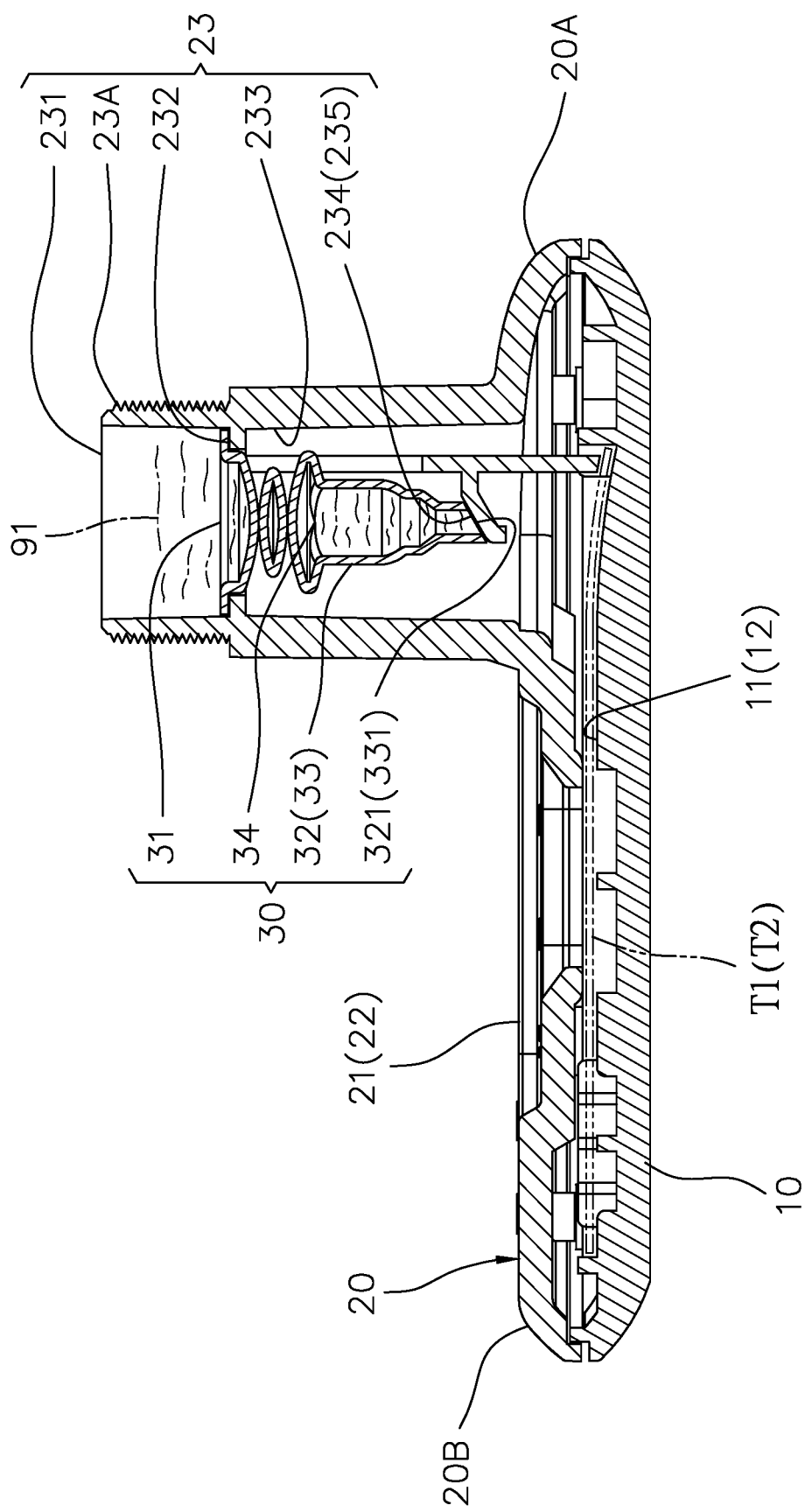
FIG. 3E is another cross-sectional view taken along the line ME-ME of FIG. 2.
Figure 4:
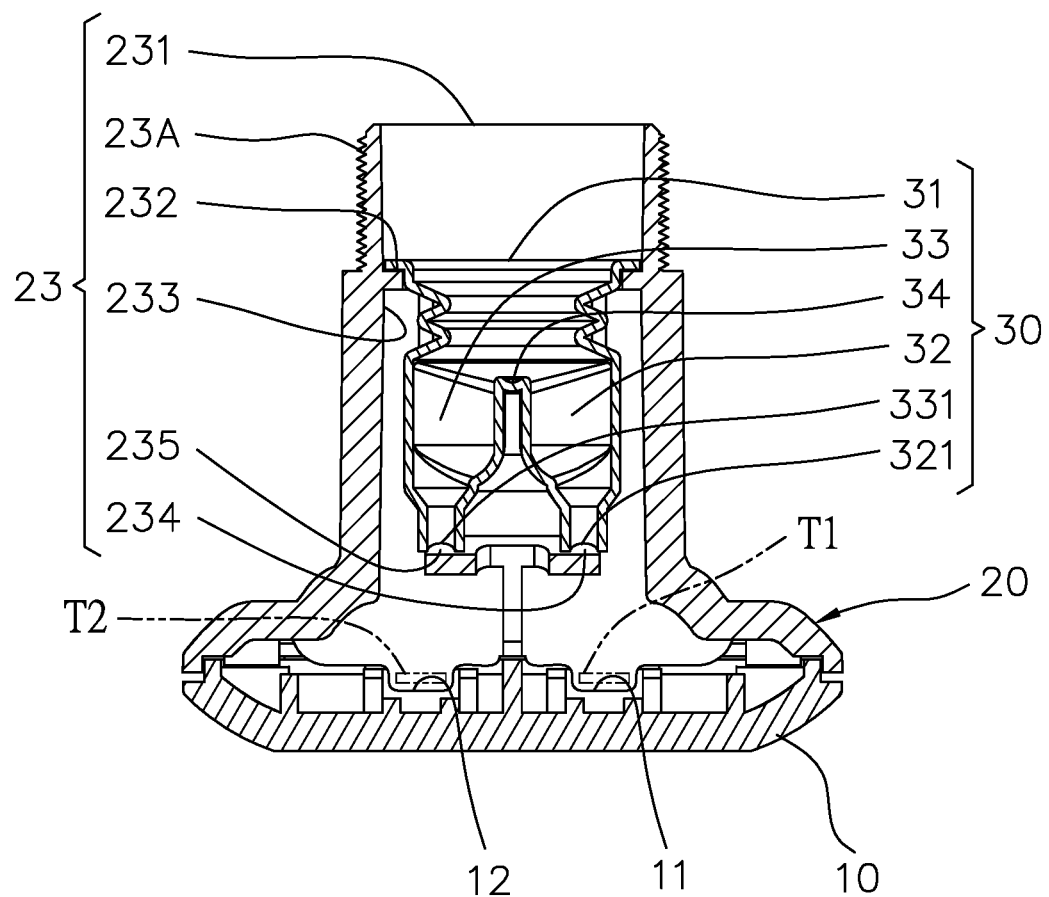
FIG. 4 is a cross-sectional view taken along the line IV-IV of FIG. 2.
Figure 5:
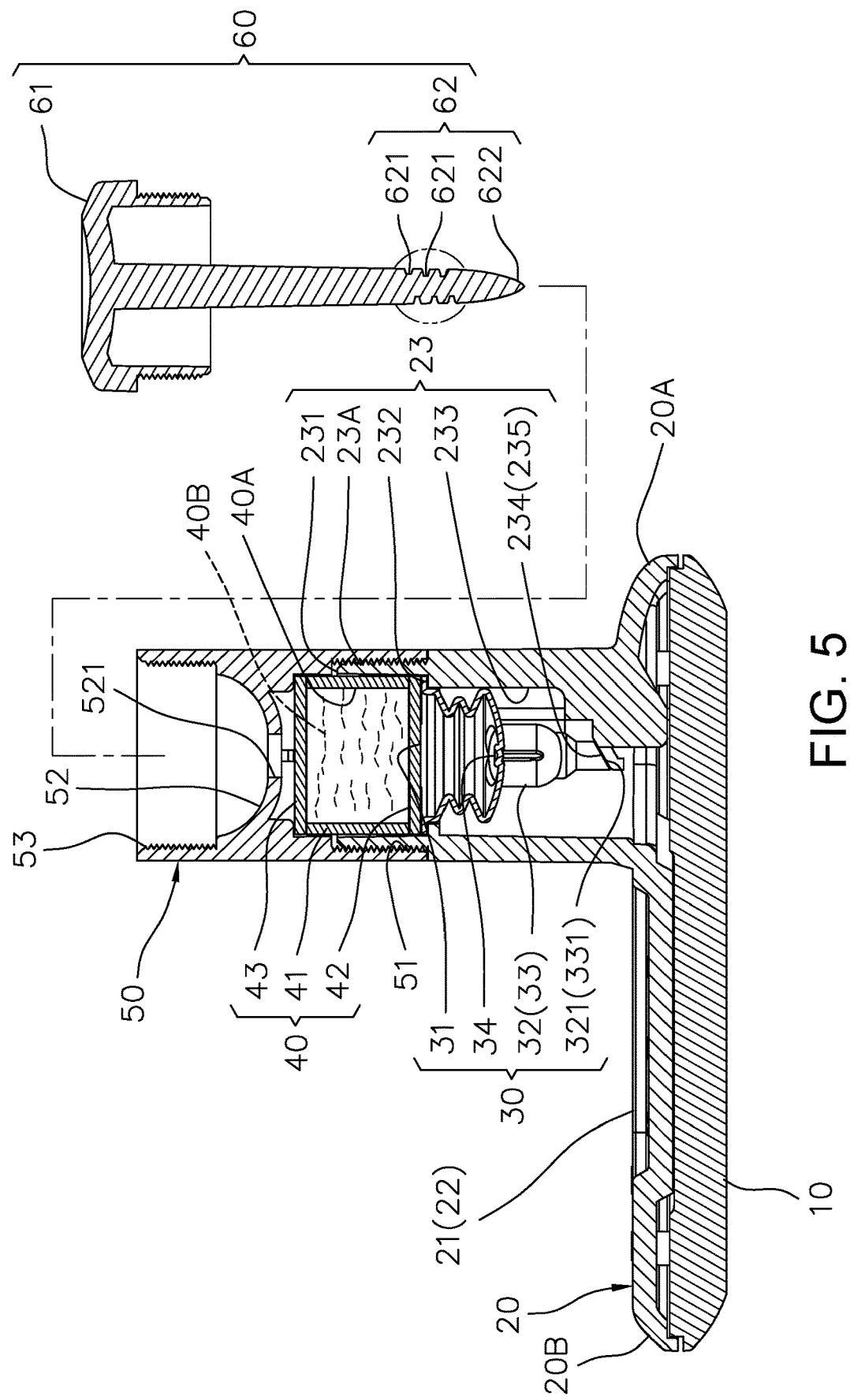
FIG. 5 is a cross-sectional view illustrating the second preferred embodiment of the present invention.

The top opening 231 is engageable with the cover 61. The top opening 231 has a connecting portion 23A which can be threaded with the top opening 231 and to generate the downward force P (as the right portion in FIG. 3D) during a threading process, as illustrated in FIG. 3D (the process is from the left to the right).

The specimen 91 could be urine or certain liquid.

Figure 6B:
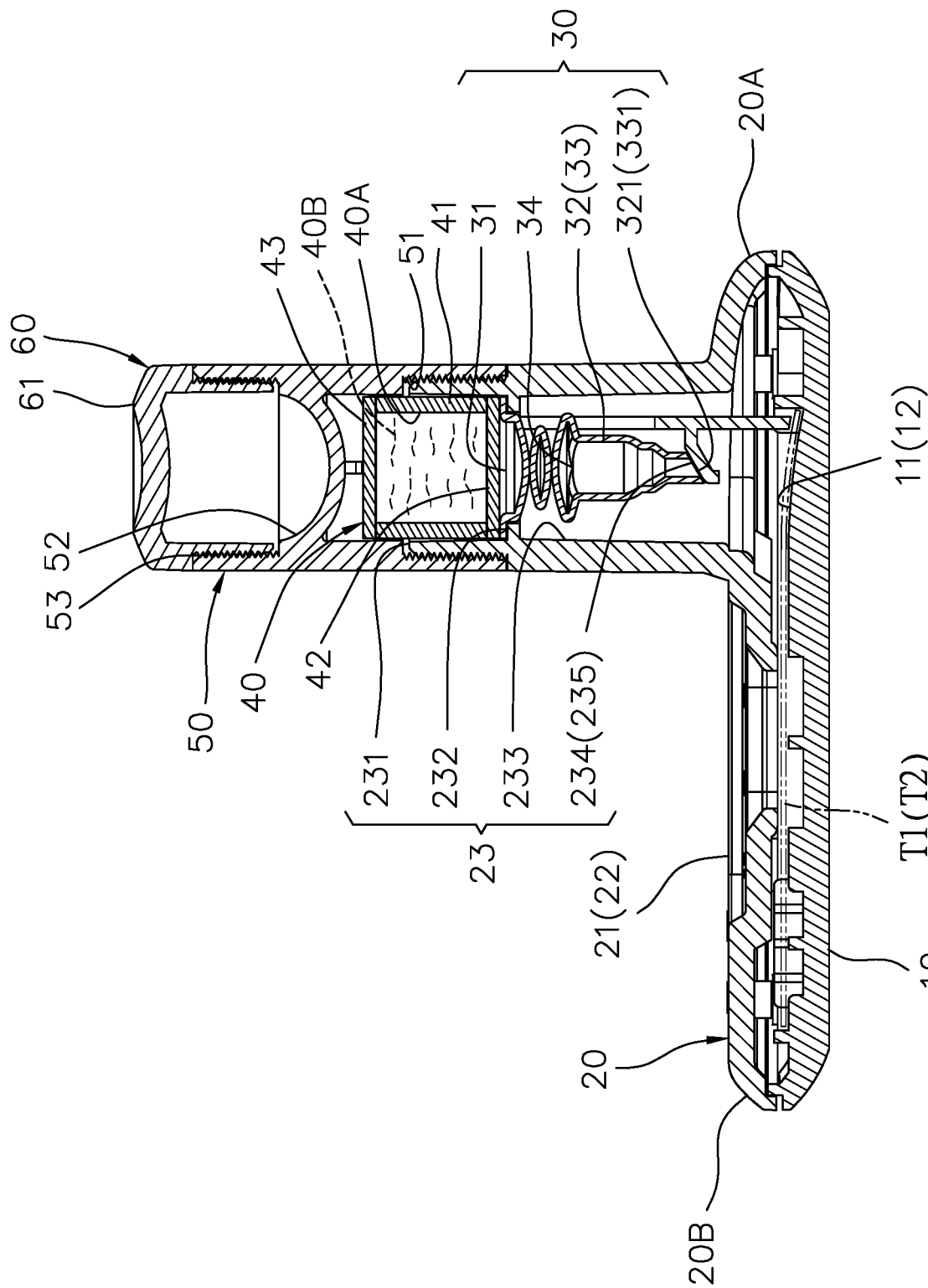
FIG. 6B is another cross-sectional view showing (similar to the viewing direction in FIG. 3E) the assembled structure of the embodiment in FIG. 5.
Figure 7:
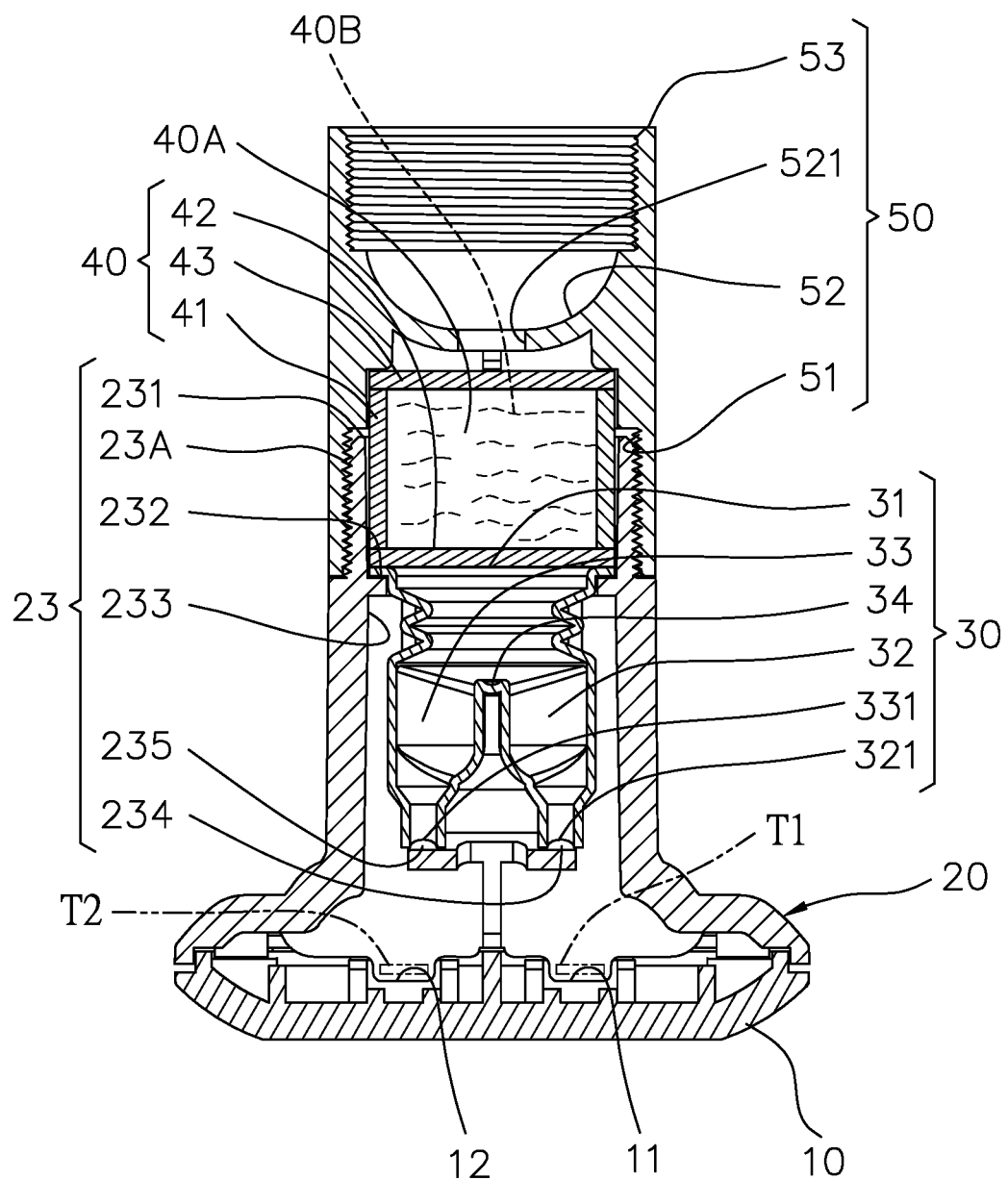
FIG. 7 is cross-sectional view (similar to the viewing direction in FIG. 4) of the assembled structure of the second preferred embodiment in FIG. 5.

With regard to the second preferred embodiment of the preset invention, the reacting device of dual path synchronous immunochromatographic platform can further comprise a solvent portion 40 and a processing portion 50. Please see FIGS. 5, 6A, 6B, and 7. However, the sampling rod 62 is omitted (not shown) in FIGS. 6A, 6B and 7.

About the solvent portion 40, it is disposed on the fluid dividing funnel 30. The solvent portion 40 including a casing 41, a lower sealing film 42, and an upper sealing film 43. The casing 41 can be sealed by the lower sealing film 42 and the upper sealing film 43. The lower sealing film 42 and the upper sealing film 43 form a first space 40A for storing a solvent 40B.

This processing portion 50 is disposed on the solvent portion 40. The processing portion 50 includes a lower securing portion 51, a funnel-like recess portion 52, and an upper securing portion 53. Furthermore, the funnel-like recess portion 52 has a through hole 521 for connecting with the upper sealing film 43. The lower securing portion 51 is provided for the processing portion 50 connecting with the hollow pipe portion 23.

In addition, the sampling rod 62 preferably includes at least one annular storing recess 621 and a sting portion 622.

So, the annular storing recess 621 is provided for storing the specimen 91. After the cover 61 engaging with the upper securing portion 53, the sting portion 622 moves through the through hole 521 and then punctures the upper seal film 43 and the lower seal film 42. Meanwhile, it can apply the downward force P on the force bearing portion 34. When the sting portion 622 moves through the through hole 521, the excess specimen 91 will stay in the funnel-like recess portion 52 (as illustrated in FIG. 6A). The specimen 91 stored in the at least one annular storing recess 621 is able to be solved in the solvent 40B and flows down into the fluid dividing funnel 30 from the first space 40A. The first fluid exit 321 and the second fluid exit 322 press on the first sloped structure 234 and the second sloped structure 235 respectively. After which, the reaction result is observable from said first window and said second window respectively. This observing portion (referring to the first preferred embodiment) has been described above, so it is not repeated here.

The specimen 91 can be excrement (or stool) so that it is needed to be solved in the solvent 40B.

Furthermore, the present invention can perform the following two test (or screening) modes.

[a] Semi-quantitative test mode (such as the specimen is excrement):

The hemoglobin (Hb) is the target to be detected so as to conduct a fecal occult blood for colorectal cancer.

Figure 8A:
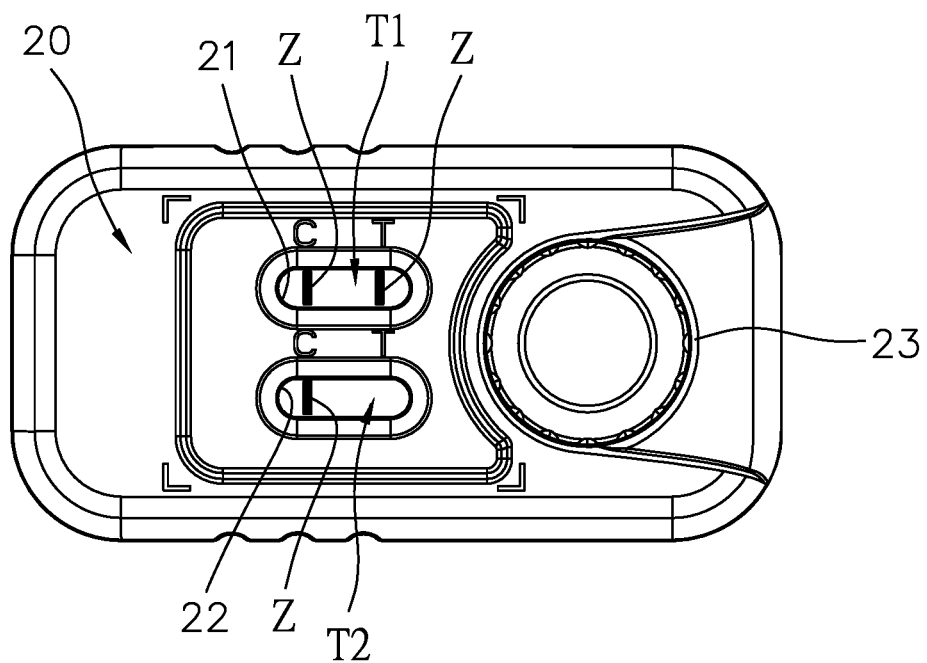
FIG. 8A illustrates one condition (low threshold) for the application in fecal occult blood test.

The first immunochromatographic carrier T1 is disposed with a low threshold (assuming 50 ng/mL) in the test area (T) portion. The second immunochromatographic carrier T2 is disposed with a high threshold (assuming 200 ng/mL) in the test area (T) portion. If the specimen (the specimen 91 already solved in the solvent 40B) contains 50 ng/mL hemoglobin (Hb), as shown in FIG. 8A, there is a confirmed reaction Z in the test area (T) and another confirmed reaction Z in the control area (C) of the first immunochromatographic carrier T1 (both the control area (C) and the test area (T) have coloring reactions that are observable by the inspector's eyes). But, in the second immunochromatographic carrier T2 with the high threshold, only the control area (C) has coloring reaction (has a confirmed reaction Z). The test area (T) has no any coloring reaction.

The result means that the hemoglobin (Hb) is larger than or equal to 50 ng/mL but less than 200 ng/mL during this fecal occult blood test.

Figure 8B:
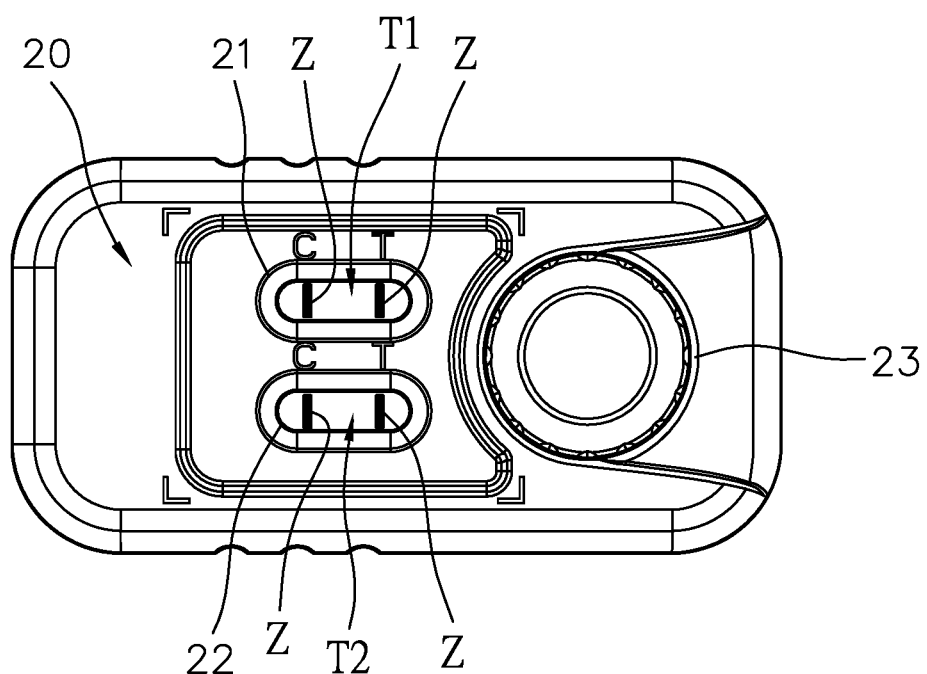
FIG. 8B illustrates another condition (high threshold) for the application in fecal occult blood test.

If the hemoglobin (Hb) of the specimen 91 is higher than 200 ng/mL, both the test area (T) in the first immunochromatographic carrier T1 and the test area (T) in the second immunochromatographic carrier T2 have coloring reactions (two confirmed reactions Z) as illustrated in FIG. 8B.

Figure 9A:
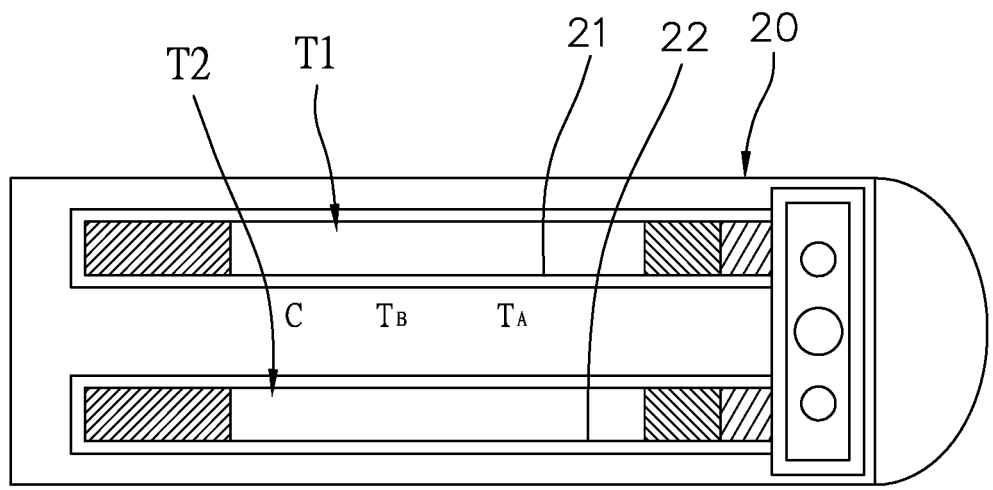
FIG. 9A is a view illustrating the condition before testing the microalbumin and Bence-Jones protein of the present invention.

[b] Semi-quantitative plus qualitative test mode (such as the specimen is urine): For example, the multiple myeloma patient's urine contains certain microalbumin and Bence-Jones protein (briefly referred as BJP; that includes κ protein and λ protein). As illustrated in FIG. 9A, it illustrates the condition before testing the microalbumin and Bence-Jones protein of the present invention.

The first immunochromatographic carrier T1 is disposed with a low threshold test area ($T_A$) and a qualitative test area ($T_B$). For example, they are microalbumin of 20 mg/L and κ protein of 1.85 mg/dL.

The second immunochromatographic carrier T2 is disposed with a high threshold test area ($T_A$) and another qualitative test area ($T_B$). For example, they are microalbumin of 200 mg/L and λ protein of 5 mg/dL.

Figure 9B:
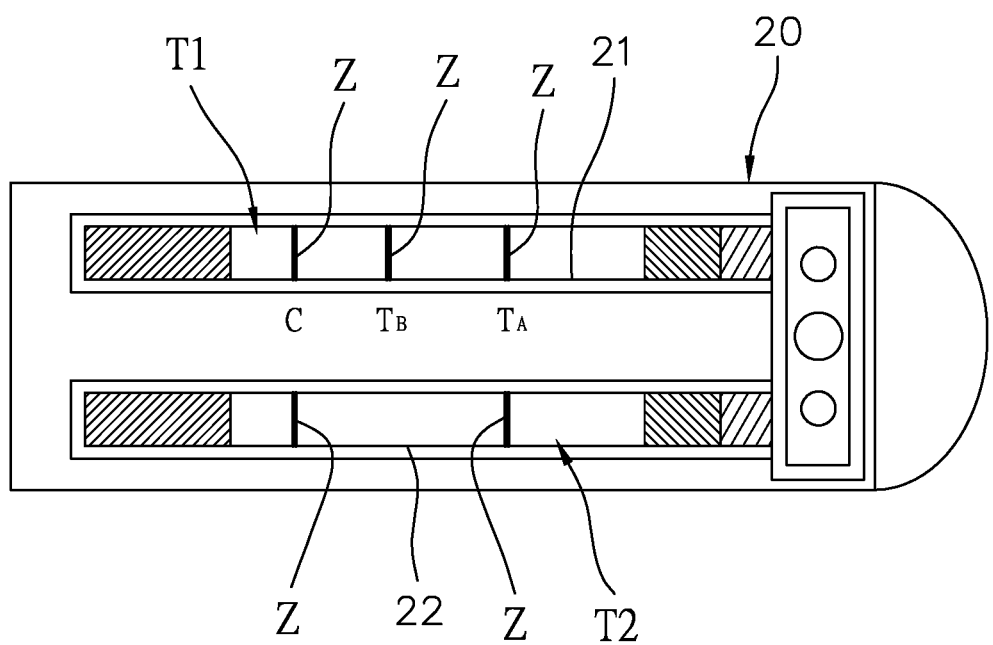
FIG. 9B is a view illustrating the condition after testing the microalbumin and Bence-Jones protein of the present invention.

After the reaction is done, as shown in FIG. 9B, there are three confirmed reactions Z at the control area (C), the low threshold test area ($T_A$) and a qualitative test area ($T_B$) of the first immunochromatographic carrier T1.

However, there are two confirmed reactions Z at the control area (C) and the low threshold test area ($T_A$) of the second immunochromatographic carrier T2. But there is no any confirmed reaction Z at the qualitative test area ($T_B$) of the second immunochromatographic carrier T2.

This test (or screening) result means that the microalbumin is higher than or equal to 200 m/L; the κ protein is positive, but the λ protein is negative. As a result, it is possible this person has multiple myeloma.

Of course, the above cases are just exemplary, other specimen 91 may contain different testing threshold and object depending on its medical application field.

Figure 10:
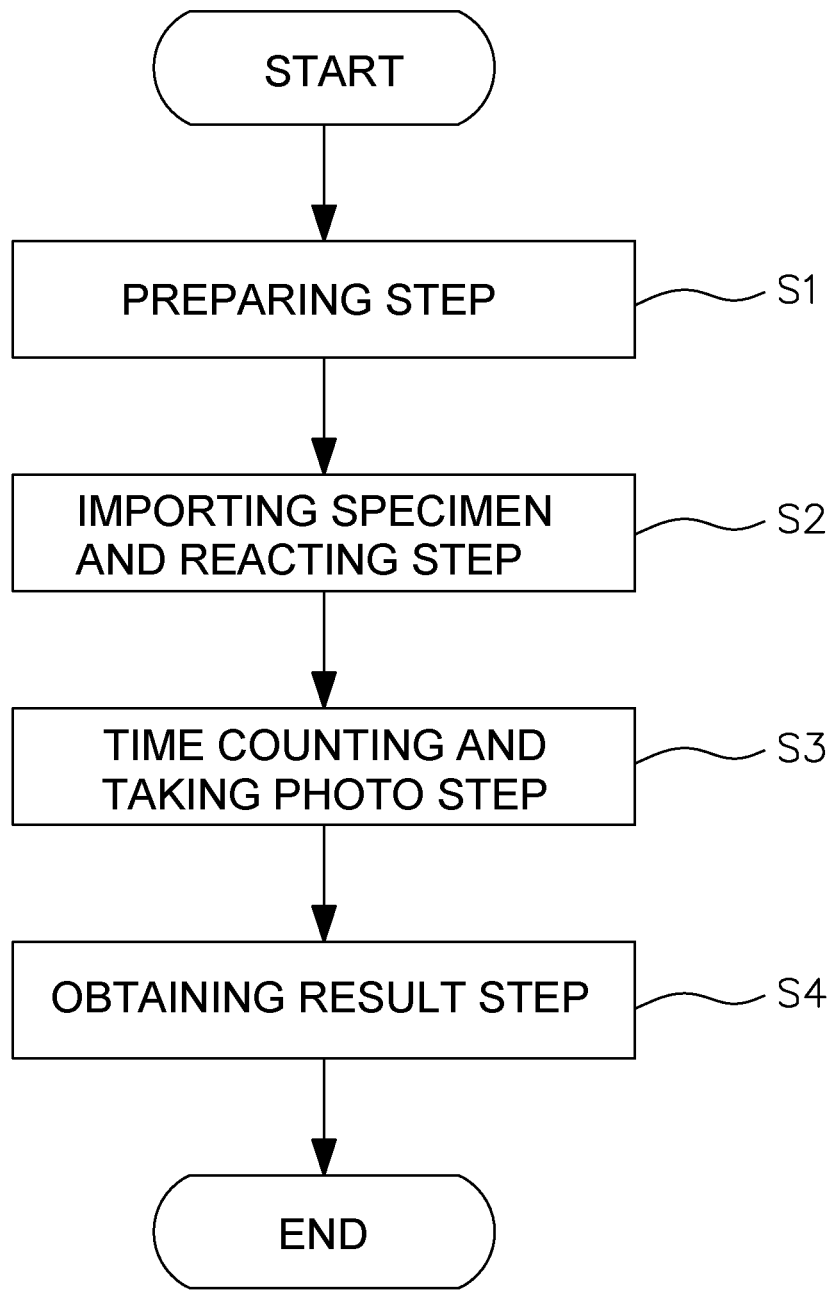
FIG. 10 shows a flowchart of the present invention.

Referring to FIG. 10, it shows a flowchart illustrating the using method of the present invention. About the using method, it comprises the following steps.

[1] a preparing step S1: preparing a seat 10, an upper housing 20, and a fluid dividing funnel 30. The seat 10 has a first slot 11 and a second slot 12. The first slot 11 is provided for receiving a first immunochromatographic carrier T1. The second slot 12 is provided for receiving a second immunochromatographic carrier T2. The upper housing 20 is disposed on the seat 10. The upper housing 20 includes a first window 21, a second window 22, a hollow pipe portion 23, a first end 20A, and a second end 20B. The first window 21, the second window 22, and the hollow pipe portion 23 are positioned between the first end 20 A and the second end 20B. The first window 21 is disposed on the first slot 11. The second window 22 is disposed on the second slot 12. The hollow pipe portion 23 is adjacent to the first end 20 A and has a top opening 231, a securing protrusion 232, an inner space 233, a first sloped structure 234, and a second sloped structure 235. This fluid dividing funnel 30 is secured on the securing protrusion 232 through the top opening 231 and extending into the inner space 233. The fluid dividing funnel 30 has a fluid entrance 31, a first diversion channel 32, a second diversion channel 33, and a force bearing portion 34. The first diversion channel 32 is disposed on and guided to the first sloped structure 234. The first diversion channel 32 has a first fluid exit 321. Similarly, the second diversion channel 33 is disposed on and guided to the second sloped structure 235. The second diversion channel 33 has a second fluid exit 331. The force bearing portion 34 is disposed between the first diversion channel 32 and the second diversion channel 33.

[2] importing specimen and reacting step S2: a specimen 91 is imported into the fluid entrance 31. By applying a downward force P (referring to FIG. 3D, from the left to right, showing the change before applying force, during applying force and after applying the force; a first height H1 is decreased into a second height H2 during the force applying process). The force bearing portion 34 is pressed down, so that the first fluid exit 321 and the second fluid exit 322 move towards the first sloped structure 234 and the second sloped structure 235 respectively. Then, both of the first fluid exit 321 and the second fluid exit 322 are effectuated to deform and slide so as to extend out portionally (as illustrated in the right portion of FIG. 3D). Therefore, the specimen 91 can drop from the first fluid exit 321 and the second fluid exit 322 to the first immunochromatographic carrier T1 and the second immunochromatographic carrier T2 respectively for reaction.

Figure 11:
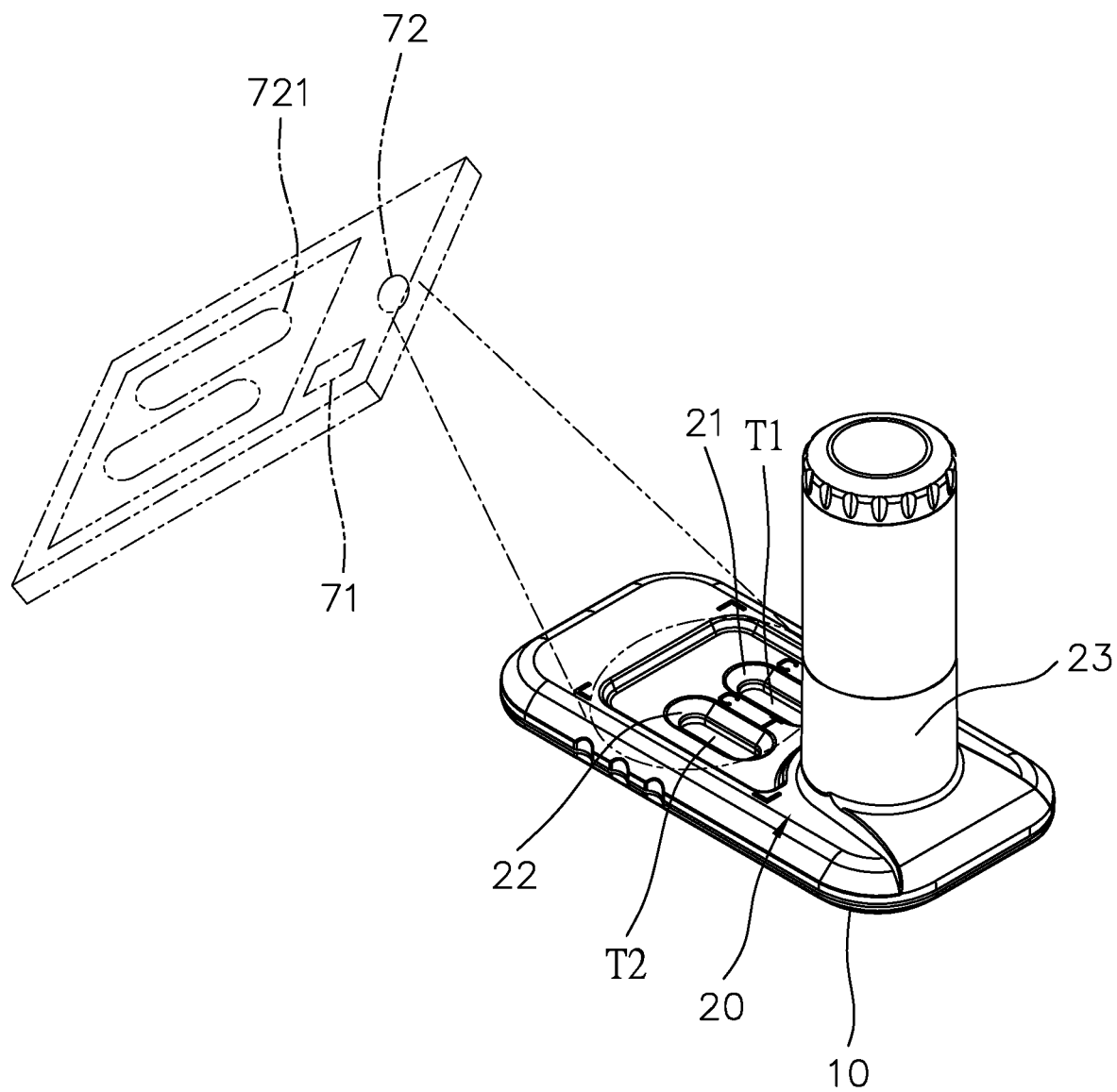
FIG. 11 is a view exhibiting the process for time counting and taking photo of the present invention.

[3] time counting and taking photo step S3: After a reacting time of the specimen(s) on the first immunochromatographic carrier T1 and the second immunochromatographic carrier T2 is reached via a time counting module 71 (as shown in FIG. 11), a reaction result is observable from the first window 21 and the second window 22 respectively. This reaction result also can be recorded via an image capturing module 72 so as to obtain a reacting result image 721.

[4] obtaining result step S4: a reaction result is obtained from the reacting result image 721.

About the second embodiment of the using method of the present invention, it comprises the following steps.

[1] a preparing step S1: preparing a seat 10, an upper housing 20, a fluid dividing funnel 30, a solvent portion 40, a processing portion 50, and a sampler 60. The seat 10 has a first slot 11 and a second slot 12. The first slot 11 is provided for receiving a first immunochromatographic carrier T1. The second slot 12 is provided for receiving a second immunochromatographic carrier T2. The upper housing 20 is disposed on the seat 10. The upper housing 20 includes a first window 21, a second window 22, a hollow pipe portion 23, a first end 20A, and a second end 20B. The first window 21, the second window 22 and the hollow pipe portion 23 are positioned between the first end 20 A and the second end 20B. The first window 21 is disposed on the first slot 11. The second window 22 is disposed on the second slot 12. The hollow pipe portion 23 is adjacent to the first end 20 A and has a top opening 231, a securing protrusion 232, an inner space 233, a first sloped structure 234, and a second sloped structure 235. This fluid dividing funnel 30 is secured on the securing protrusion 232 through the top opening 231 and extending into the inner space 233. The fluid dividing funnel 30 has a fluid entrance 31, a first diversion channel 32, a second diversion channel 33, and a force bearing portion 34. The first diversion channel 32 is disposed on and guided to the first sloped structure 234. The first diversion channel 32 has a first fluid exit 321. Similarly, the second diversion channel 33 is disposed on and guided to the second sloped structure 235. The second diversion channel 33 has a second fluid exit 331. The force bearing portion 34 is disposed between the first diversion channel 32 and the second diversion channel 33. About the solvent portion 40, it is disposed on the fluid dividing funnel 30. The solvent portion 40 including a casing 41, a lower sealing film 42, and an upper sealing film 43. The casing 41 can be sealed by the lower sealing film 42 and the upper sealing film 43 and form a first space 40A for storing a solvent 40B. This processing portion 50 is disposed on the solvent portion 40. The processing portion 50 includes a lower securing portion 51, a funnel-like recess portion 52, and an upper securing portion 53. Furthermore, the funnel-like recess portion 52 has a through hole 521 for connecting with the upper sealing film 43. The lower securing portion 51 is provided for the processing portion 50 connecting with the hollow pipe portion 23. The sampler 60 can apply a downward force P. The sampler 60 contains a cover 61 and a sampling rod 62 (that is shown in FIG. 6A, but not shown in FIGS. 6B and 7). The sampling rod 62 (extended from the cover 61) includes at least one annular storing recess 621 and a sting portion 622.

[2] importing specimen and reacting step S2: the at least one annular storing recess 621 stores the specimen 91. After the cover 61 engages with said upper securing portion 53, the sting portion 622 moves through the through hole 521 and punctures the upper sealing film 43 and the lower sealing film 42, and then apply the downward force P on the force bearing portion 34. When the sting portion 622 moves through the through hole 521, excess specimen 91 is stayed in the funnel-like recess portion 52 (as shown in FIG. 6A), the specimen 91 stored in the at least one annular storing recess 621 is able to be solved in the solvent 40B and flows down into the fluid dividing funnel 30. The force bearing portion 34 is pressed down, so that the first fluid exit 321 and the second fluid exit 322 move towards the first sloped structure 234 and the second sloped structure 235 respectively. Then, both of the first fluid exit 321 and the second fluid exit 322 are effectuated to deform and slide so as to extend out portionally (as illustrated in the right portion of FIG. 3D). Therefore, the specimen 91 (already mixed with the solvent 40B) can drop from the first fluid exit 321 and the second fluid exit 322 to the first immunochromatographic carrier T1 and the second immunochromatographic carrier T2 respectively for reaction.

[3] time counting and taking photo step S3: After a reacting time of the specimen(s) on the first immunochromatographic carrier T1 and the second immunochromatographic carrier T2 is reached via a time counting module 71 (as shown in FIG. 11), a reaction result is observable from the first window 21 and the second window 22 respectively. And, this reaction result also can be recorded via an image capturing module 72 so as to obtain a reacting result image 721.

[4] obtaining result step S4: a reaction result is obtained from the reacting result image 721.

The advantages and functions of the present invention can be summarized as follows.

[1] The fluid dividing funnel can divide the specimen into two immunochromatographic carriers evenly. Because there are two fluid exits in this invention, the specimen will be distributed into two corresponding immunochromatographic carriers evenly.

[2] The sloped structure can increase the accuracy of specimen supply. This invention has the unique design of the first sloped structure and the second sloped structure. It makes sure to guide the specimen dropping down to the first immunochromatographic carrier and the second immunochromatographic carrier. So, both immunochromatographic carriers have sufficient volume of specimen to be reacted or tested. Thus, the sloped structures can increase the accuracy of specimen supply.

[3] Excess specimen can be scraped off for enhancing the solving accuracy. The volume of the specimen stored in the at least one annular storing recess might be different depending on different users' sample collecting ways. If there is too much specimen attached on the sampling rod, the excess specimen will be scraped off during the sapling rod passing through the through hole and stay in the funnel-like recess portion. Thus, the solving accuracy will be raised by blocking out extra unnecessary specimen.

[4] It can decrease the possibility of false positive problem. The threshold setting of the immunochromatographic method is related to the clinical disease screening. Therefore, if the volume of the specimen is different, it will change or interfere the concentration of the specimen to be tested. So, it might cause the false positive problem. If there is too much specimen solved in the solvent, its concentration will become higher so as to cause the false positive problem. Thus, it can decrease the possibility of false positive problem significantly.

What is claimed is:

1. A reacting device of dual path synchronous immunochromatographic platform comprising:

a seat having a first slot and a second slot, said first slot being provided for receiving a first immunochromatographic carrier, said second slot being provided for receiving a second immunochromatographic carrier;

an upper housing disposed on said seat, said upper housing including a first window, a second window, a hollow pipe portion, a first end, and a second end; said first window, said second window and said hollow pipe portion being positioned between said first end and said second end, said first window being disposed on said first slot; said second window being disposed on said second slot; said hollow pipe portion being adjacent to said first end and having a top opening, a securing protrusion, an inner space, a first sloped structure, and a second sloped structure; and a fluid dividing funnel being secured on said securing protrusion through said top opening and extending into said inner space, said fluid dividing funnel having a fluid entrance, a first diversion channel, a second diversion channel, and a force bearing portion; said first diversion channel being disposed on and guided to said first sloped structure, said first diversion channel having a first fluid exit; said second diversion channel being disposed on and guided to said second sloped structure, said second diversion channel having a second fluid exit; said force bearing portion being disposed between said first diversion channel and said second diversion channel;

wherein a specimen is imported into said fluid entrance and said force bearing portion is pressed down so that said first fluid exit and said second fluid exit move towards said first sloped structure and said second sloped structure respectively and said first fluid exit and said second fluid exit being effectuated to deform and slide so as to extend out portionally; said specimen drops from said first fluid exit and said second fluid exit to said first immunochromatographic carrier and said second immunochromatographic carrier respectively; and a reaction result is observable from said first window and said second window respectively;

wherein said fluid dividing funnel is a flexible structure; and further comprising:

a pressing element for applying a downward force on force bearing portion; said pressing element is a sampler;

wherein said sampler contains a cover and a sampling rod that is extended from said cover so as to allow for applying said downward force toward said force bearing portion;

wherein said top opening is engageable with said cover, said top opening has a connecting portion which is able to be threaded with said top opening and to generate said downward force during a threading process;

a solvent portion disposed on said fluid dividing funnel, said solvent portion including a casing, a lower sealing film, and an upper sealing film; said casing being sealed by said lower sealing film and said upper sealing film and forming a first space for storing a solvent; and a processing portion disposed on said solvent portion, said processing portion including a lower securing portion, a funnel-like recess portion, and an upper securing portion; said funnel-like recess portion having a through hole for connecting with said upper sealing film, said lower securing portion being provided for said processing portion connecting with said hollow pipe portion;

said sampling rod including at least one annular storing recess and a sting portion;

wherein said annular storing recess is stored said specimen, after said cover engaging with said upper securing portion, said sting portion moving through said through hole and puncturing said upper seal film and said lower seal film, and then apply said downward force on said force bearing portion; when said sting portion moving through said through hole, excess specimen being stayed in said funnel-like recess portion, said specimen stored in said at least one annular storing recess being able to be solved in said solvent and flowing down into said fluid dividing funnel from said first space, said first fluid exit and said second fluid exit pressing said first sloped structure and said second sloped structure respectively.

2. The reacting device of dual path synchronous immunochromatographic platform as claimed in claim 1, wherein:

said first immunochromatographic carrier is a test paper; and said second immunochromatographic carrier is another test paper.

* * * * *